United States Patent [19]

Earley et al.

[11] Patent Number: 4,777,169

[45] Date of Patent: Oct. 11, 1988

[54] BENZODIAZEPINE DERIVATIVES

[75] Inventors: James V. Earley, Cedar Grove; Norman W. Gilman, Wayne, both of N.J.

[73] Assignee: Hoffmann-La Roche Inc., Nutley, N.J.

[21] Appl. No.: 117,599

[22] Filed: Nov. 6, 1987

Related U.S. Application Data

[63] Continuation-in-part of Ser. No. 77,472, Jul. 24, 1987, abandoned.

[51] Int. Cl.[4] ............... A61K 31/55; C07D 243/24; C07D 243/26

[52] U.S. Cl. ................................. 514/221; 540/507
[58] Field of Search .................. 540/507; 514/221

[56] References Cited

U.S. PATENT DOCUMENTS 3,176,009  3/1965  Bell ........................ 540/507
4,083,948  4/1978  Davis et al. ............... 540/507

Primary Examiner—Robert T. Bond
Attorney, Agent, or Firm—Jon S. Saxe; George M. Gould; Julie M. Prlina

[57] ABSTRACT

Benzodiazepine derivatives useful in immunoassays for benzodiazepines.

16 Claims, No Drawings

BENZODIAZEPINE DERIVATIVES

CROSS-REFERENCE TO RELATED APPLICATIONS

This application is a continuation-in-part of U.S. patent application Ser. No. 077,472 filed July 24, 1987.

BACKGROUND OF THE INVENTION

Published surveys show that no less than one in ten adult Americans takes a benzodiazepine tranquilizer or hypnotic in a year's time. These compounds are prescribed to treat a wide variety of conditions, for example, neurotic anxiety, depression, insomnia, muscle spasm, and countless functional disorders ranging from headaches to dyspareunia. (*Benzodiazepines in Clinical Medicine*, Greenblatt and Shader, Raven Press, 1974, v).

After therapeutic doses of benzodiazepines, only trace amounts are present in body fluids due to extensive biotransformation and tissue distribution. Therefore, very sensitive methods are needed to enable quantitation of benzodiazepines in tissue and body fluids.

A variety of screening procedures exist for the detection of benzodiazepines in blood, urine, or body fluids. Thin layer chromatography (TLC) or gas liquid chromatography (GLC) or spectrophotofluorometry have been used. More recently immunoassays utilizing antibodies to benzodiazepines have been developed and have proved to be very effective in quantitating minute amounts of benzodiazepines in body fluids. In this technology it is particularly necessary to have a compound which acts as a substrate upon which the "tracer" (which enables detection and quantitation of the unknown analyte) may bind. Various benzodiazepine derivatives have been used for this purpose. See U.S. Pat. No. 4,083,948 by Davis et al. which describes Benzodiazepine Radioimmunoassays Using $I^{125}$ Labels attached to benzodiazepine derivative substrate molecules.

SUMMARY OF THE INVENTION

The instant invention comprises novel Benzodiazepine derivative compounds. The instant invention also comprises radiolabelled novel Benzodiazepine derivative compounds.

The instant invention also comprises the use of the compounds of the invention in immunoassays to detect the presence of benzodiazepines.

DETAILED DESCRIPTION

The instant invention comprises compounds of the formula

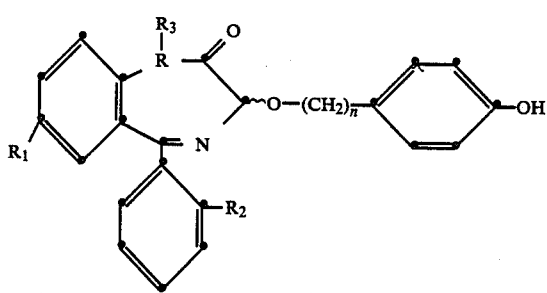

wherein $R_1$ is halogen or nitro; $R_2$ is hydrogen or halogen; and $R_3$ is hydrogen or lower alkyl; and n=2-6.

The instant invention also comprises compounds of the above formula which have been radiolabelled. The Formula I compounds lend themselves easily to radiolabelling. The radioactive molecules attach to either the 3 position or the 5 position or both positions of the hydroxyphenyl portion of the Formula I compound. Preferred is where the compounds have been radiolabelled with $I^{125}$.

Particularly preferred is a compound of Formula I wherein $R_1$ is Cl; $R_2$ is H; $R_3$ is H; and n is 2 said compound having the formula

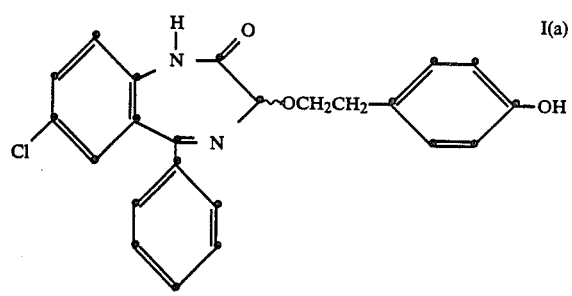

Also particularly preferred is a compound of formula I(a) which has been radiolabelled. The radioactive molecule attaches to the 3 position of the 5 position or both positions on the hydroxyphenyl portion of the Formula I(a) compound. Most preferred is a compound of Formula I(a) which has been radiolabelled with $I^{125}$ wherein said compound is $I^{125}$-7-chloro-3-[2-(4-hydroxyphenyl)]ethoxy-5-phenyl-1,3-dihydro-2H-1,4-benzodiazepine-2-one.

The intermediates used in the manufacture of the compounds of Formula I are known, said intermediates having the general formula

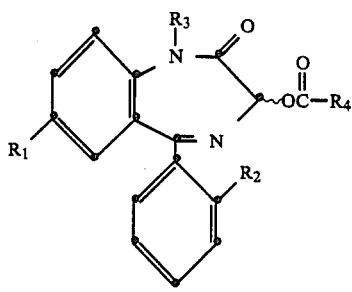

wherein $R_1$ is halogen or nitro; $R_2$ is hydrogen or halogen; $R_3$ is hydrogen or lower alkyl; and $R_4$ is lower alkyl or halogen substituted lower alkyl.

Particularly the intermediate is a compound of Formula II wherein $R_1$ is Cl; $R_2$ is H; $R_3$ is H; and $R_4$ is $CH_3$ said compound having the formula

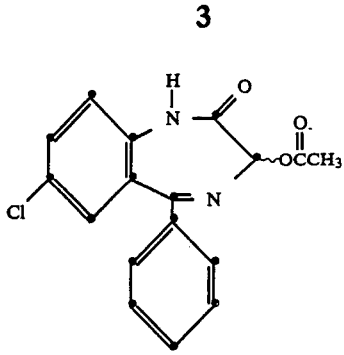

The Formula I compounds may be manufactured by placing Formula II compound and 4-hydroxyphenethylalcohol in dry N, N-dimethylformamide. This solution is kept cold and stirred while hydrogen chloride gas is bubbled into the solution. The mixture is then allowed to stand at room temperature. The reaction mixture is again cooled and the pH adjusted from 7.1 to 7.9 with base. The mixture is then filtered and the gummy precipitate stirred with dichloromethane and water then filtered. The solid is crystallized from a mixture of dichloromethane and methanol to yield the compound of Formula I.

The invention also comprises the use of the radiolabelled formula I compounds in immunoassays to detect the presence of benzodiazepines.

Particularly preferred is where the Formula I compound is radiolabelled with $I^{125}$. Particularly preferred is where the $I^{125}$ labelled Formula I compound is $I^{125}$-7-chloro-3-[2-(4-hydroxyphenyl)ethoxy)-5-phenyl-1,3-dihydro-2H-1,4-benzodiazepine-2-one.

The preferred radioimmunoassay for the detection of benzodiazepines is of the competitive binding type. The Formula I compounds are first radiolabelled according to methods known in the art. Preferred is where the Formula I compounds are radiolabelled with $I^{125}$ in accordance with the methods set forth in U.S. Pat. No. 4,083,948 to yield the $I^{125}$ derivative. Particularly preferred is where the radiolabelled Formula I compound $I^{125}$-7-chloro-3-[2-(4-hydroxyphenyl)ethoxy)-5-phenyl-1,3-dihydro-2H-1,4-benzodiazepine-2-one is utilized in the radioimmunoassay to detect the presence of benzodiazepines.

The radioiodinated Formula I compound will bind antibodies against benzodiazepines. An unknown sample containing an unknown quantity of benzodiazepines or their metabolites is introduced into the system. The benzodiazepines present in the unknown will compete with the iodinated Formula I compound for the antibody allowing quantitation of the amount of benzodiazepines in the unknown. The radiolabelled Formula I compounds are then used in radioimmunoassays to detect the presence of benzodiazepines. The methodology of these radioimmunoassays is known in the art and is described in U.S. Pat. No. 4,083,948.

In one useful assay procedure, a known amount of labelled benzodiazepine is mixed with an antibody which selectively binds said benzodiazepine and a sample containing an unknown concentration of the target benzodiazepine is added. The amount of the target benzodiazepine in the sample can be determined by measuring the inhibition of the binding of the specific antibody of the labelled benzodiazepine by the sample and comparing the value observed with a standard curve previously developed. The reagents may be added in any order. Other assay procedures known in the art for carrying out radioimmuno-assays can also be employed.

The present invention will be further described in connection with the following example which is set forth for purposes of illustration only.

EXAMPLE 1

Preparation of 7-Chloro-3-[2-(4-hydroxyphenyl)ethoxy)-5-Phenyl-1,3-dihydro-2H-1,4-benzodiazepine-2-one A solution of 10.0 grams (0.0309 mol) of 3-acetoxy-7-chloro-5-phenyl-1,3-dihydro-2H-1,4-benzodiazepine-one and 11.0 grams (0.080 mol) of 4-hydroxyphenethylalcohol (Aldrich) in 50 ml. dry N,N-dimethylformamide was stirred in an ice bath and hydrogen chloride gas was bubbled into the solution for 5-10 minutes. After standing at room temperature for 18 hours, the reaction mixture was poured onto ice and the pH adjusted to 7.5 with ammonium hydroxide. The mixture was filtered and the gummy precipitate was stirred with 50 ml. dichloromethane and 50 ml. water for 5 minutes and filtered. The solid was crystallized from a mixture of dichloromethane and methanol to give 9.6 grams (77%) of the compound of Formula I (a) as white rods, m.p. 222°-230° C.; 1R (KBr) 3310, 3215, 3140, (OH,NH), 1685 cm$^{-1}$ (C=O); NMR (DMSO-d$_6$) 2.86 (t, 2H, CH$_2$Ar), 3.77, 3.95 (2q, 2H, CH$_2$O), 4.78 (s, 1H, CH), 6.68, 7.09 (2d, 4H, aromatics), 9.18 (s, 1H, OH), 10.81 (s, 1H, NH); mass spectrum m/e 406 (M+) *Anal.* Calcd for C$_{23}$H$_{19}$ClN$_2$O$_3$: C, 67.90; H, 4.71; N, 6.89. Found: C, 67.91; H, 4.83; N, 6.80.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. A compound of the formula

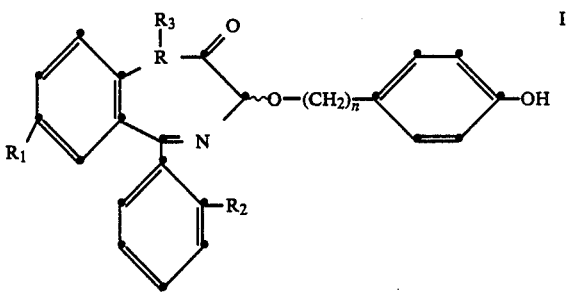

wherein R$_1$ is halogen or nitro; R$_2$ is hydrogen or halogen; and R$_3$ is hydrogen or lower alkyl and n=2-6.

2. The compound of claim 1 wherein R$_1$ is halogen.
3. The compound of claim 2 wherein R$_2$ is hydrogen.
4. The compound of claim 3 wherein R$_3$ is hydrogen.
5. The compound of claim 4 wherein n=2.
6. The compound of claim 5 wherein R$_1$ is Cl; said compound having the formula

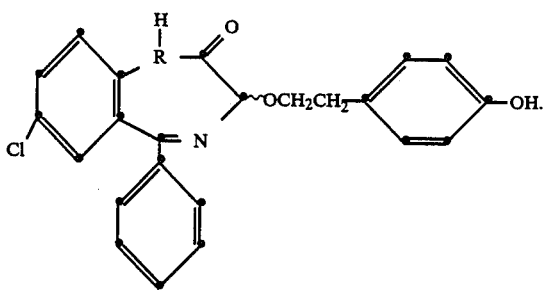
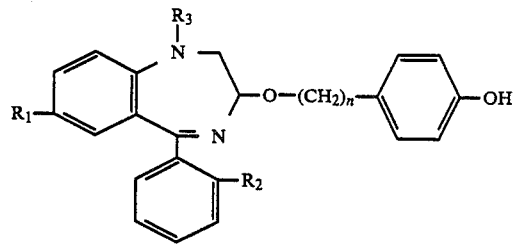

wherein $R_1$ is halogen or nitro; $R_2$ is hydrogen or halogen; and $R_3$ is hydrogen or lower alkyl and n=2-6.

7. The compound of claim 1 which is radiolabelled.

8. The compound of claim 7 wherein the compound is radiolabelled with $I^{125}$.

9. The compound of claim 8 which is radiolabelled with $I^{125}$ wherein the compound is $I^{125}$-7-chloro-3-[2-(4-hydroxyphenyl)ethoxy)-5-phenyl-1,3-dihydro-2H-1,4-benzodiazepine-2-one.

10. In a method for the radioimmunoassay for a benzodiazepine compound or metabolites thereof in a sample, which comprises mixing said sample with a known amount of a labelled benzodiazepine compound and antibody which selectively bind said benzodiazepine compound and said labelled benzodiazepine compound, measuring the degree of binding of the said labelled benzodiazepine compound to said antibody, and determining the amount of said benzodiazepine compound in said sample by comparing said degree of binding to a standard curve; the improvement which comprises utilizing a radiolabelled compound of the formula 11. The method of claim 10 wherein $R_1$ is halogen.
12. The method of claim 10 wherein $R_2$ is hydrogen.
13. The method of claim 12 wherein $R_3$ is hydrogen.
14. The method of claim 13 wherein n=2.
15. The method of claim 14 wherein $R_1$ is Cl said compound having the formula

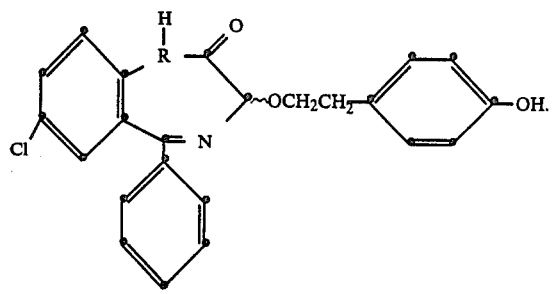

16. The method of claim 15 where the compound is radiolabelled with $I^{125}$ wherein said compound is $I^{125}$-7-chloro-3-[2-(4-hydroxyphenyl)ethoxy)-5-phenyl-1,-dihydro-2H-1,4-benzodiazepine-2-one.

* * * * *

UNITED STATES PATENT AND TRADEMARK OFFICE
CERTIFICATE OF CORRECTION

PATENT NO. : 4,777,169
DATED : October 11, 1988
INVENTOR(S) : EARLEY, et al

It is certified that error appears in the above-identified patent and that said Letters Patent is hereby corrected as shown below:

On Page 2, Column 2, Line 34:
After position delete "of" and insert therefore --or--.

Column 4, Line 27:
After C.; delete "1R" and insert therefore --IR--.

Column 6, Lines 1-10:
The structure is incorrect. The corrected structure is as set forth below.

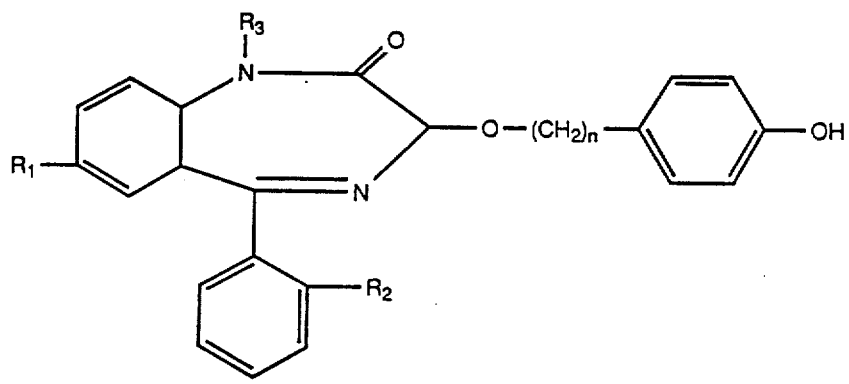

Signed and Sealed this

Eighteenth Day of April, 1989

*Attest:*

DONALD J. QUIGG

*Attesting Officer*   *Commissioner of Patents and Trademarks*